(12) United States Patent
Han et al.

(10) Patent No.: US 8,652,537 B2
(45) Date of Patent: Feb. 18, 2014

(54) HERBAL DRUG COMPOSITION FOR CARTILAGE PROTECTION

(75) Inventors: Chang-Kyun Han, Seoul (KR); Wie-Jong Kwak, Seoul (KR); Ki Won Joung, Kyunggi-do (KR); Hun Seung Yoo, Seoul (KR); Do Seung Kum, Seoul (KR); Yong-Baik Cho, Kyunggi-do (KR); Keun Ho Ryu, Seoul (KR); Hae In Rhee, Seoul (KR); Taek Su Kim, Kyunggi-do (KR); In Ho Jung, Kyunggi-do (KR); So Yoon Lee, Seoul (KR); Jung Bum Yi, Kyunggi-do (KR); Joo Hyon Kim, Seoul (KR); Key An Um, Kyunggi-do (KR)

(73) Assignee: SK Chemicals Co., Ltd., Kyunggi-do (KR)

( * ) Notice: Subject to any disclaimer, the term of this patent is extended or adjusted under 35 U.S.C. 154(b) by 0 days.

(21) Appl. No.: 13/400,784

(22) Filed: Feb. 21, 2012

(65) Prior Publication Data
US 2012/0148693 A1 Jun. 14, 2012

Related U.S. Application Data

(63) Continuation of application No. 10/478,048, filed as application No. PCT/KR02/00010 on Jan. 4, 2002, now abandoned.

(30) Foreign Application Priority Data
May 18, 2001 (KR) .................................. 2001/27231

(51) Int. Cl.
*A61K 36/00* (2006.01)

(52) U.S. Cl.
USPC ....................................................... 424/725

(58) Field of Classification Search
USPC .......................................................... 424/725
See application file for complete search history.

(56) References Cited

U.S. PATENT DOCUMENTS 5,910,307 A * 6/1999 Kwak et al. ................... 424/745

FOREIGN PATENT DOCUMENTS

| EP | 0 832 652 A1 | 4/1998 |
| EP | 0832 652 A1 * | 4/1998 |
| WO | WO 99/59606 | 11/1999 |

OTHER PUBLICATIONS

Chang et al. :Quantitation of Rosmarinic Acid in the Native Labiatae Herbs and From the Market in Taiwan; Zhonghua Yaoxue Zazhi (1989), 41 (1), pp. 49-56, one page English Abstract.*
Pulatova, T.: Polyphenol Compounds of Several Labitae Species Growing in Uzbekistan; Mater. Yubileinoi Resp. Nauchn. Konf. Farm., Posvyashch. 50-Letiyu Obraz. SSSR (1972), 35-7, one page English Abstract.*

* cited by examiner

*Primary Examiner* — Patricia Leith
(74) *Attorney, Agent, or Firm* — Frommer Lawrence & Haug LLP; Ronald R. Santucci

(57) ABSTRACT

The present invention relates to a herbal drug composition for cartilage protection comprising plant extracts of Clematis Radix, Trichosanthis Radix, and Prunellae Spica and an optimal content of rosmarinic acid to: (i) alleviate pains; (ii) inhibit the acute/chronic inflammation, platelet/whole blood aggregation, immunocyte (B-lymphcyte and T-lymphcyte) proliferation, inflammation-inducing enzyme activities, and enzyme activities associated with degradation of joint tissue; (iii) scavenge activity of toxic active oxygen radicals; and (iv) further provide excellent cartilage protection activity to be effectively used as an anti-inflammatory agent with analgesic effects, blood circulation enhancer, arthritis therapeutic agent and cartilage protective.

16 Claims, 3 Drawing Sheets

HERBAL DRUG COMPOSITION FOR CARTILAGE PROTECTION

FIELD OF THE INVENTION

The present invention relates to a herbal drug composition for cartilage protection and more particularly, to the drug composition for cartilage protection comprising plant extracts of Clematis Radix, Trichosanthis Radix, and Prunellae Spica and an optimal content of rosmarinic acid to: (i) alleviate pains; (ii) inhibit the acute/chronic inflammation, platelet/whole blood aggregation, immunocyte (B-lymphocyte and T-lymphocyte) proliferation, inflammation-inducing enzyme activities, and enzyme activities associated with degradation of joint tissue; (iii) scavenge activity of toxic active oxygen radicals; and (iv) further provide excellent cartilage protection activity to be effectively used as an anti-inflammatory agent with analgesic effects, blood circulation enhancer, arthritis therapeutic agent and cartilage protective.

BACKGROUND OF THE INVENTION

Clematis Radix, Trichosanthis Radix, and Prunellae Spica are well known for medicinal plants. Each medicinal plant has long been used for the treatment of general inflammations, such as various swellings, wounds, bronchitis, mastitis, tonsillitis, and anal fistula and also for the relief of various symptoms such as cold or numb hands, painful knees, painful waist and shoulder, feeble in health and pain in the skin, in the form of aqueous plant extract. These symptoms are similar to general arthritis including chronic rheumatism in terms of the modern pathological concept.

Clematis Radix, a root of *Clematis mandshurica* and the same genera in plant taxonomy, is distributed in the shady forest throughout Asia. It is collected in autumn, washed cleanly after removing cormophyte and root hair, chopped finely and dried in the sun to be used as a medicinal use. Clematis Radix, a non-toxic medicinal plant, has long been used for the treatment of the following symptoms: pains in the extremities; motor disturbance in knee joints; and paralysis in the extremities. In particular, Clematis Radix has been frequently used as a miraculous drug in those patients who feel uncomfortable while standing due to the coldness in waist, knees and feet. It is well known that Clematis Radix has various constituents of flavanone glycosides such as clematin, etc. and saponins such as clemontanoside A, clemontanoside B, clemontanoside C, and clemontanoside S, glucoses, and sterols [Research Archives of Useful Plants Resources in Korea, Korea Research Institute of Chemical Technology, pp 780-781 (1988), 2. An Explanatory Diagram of Korean Medicinal plants, Youngrim Pub., pp 489-490 (1990)].

Trichosanthis Radix, known as "multifarious medicine" or "Karokon", is a non-toxic medicinal herb prepared by collecting roots of *Trichosnathes kirilowii* and the same genera in plant taxonomy, which are perennial liana plants, in autumn. The outer shells of cleanly washed roots are removed and the rest of the roots are cut appropriately and dried in the sun for medicinal use. Trichosanthis Radix has been widely used for excretion of pus, vanishing the boil, detoxification and antipyretic effect and also effective for diseases symptomized by thirst, various swellings, mastitis, and anal fistula. It has been investigated up to now that Trichosanthis Radix contains trichosanthin as proteins, arginine and citruline as amino acids, and palmitic acid and linoleic acid as fatty acids. Recently Trichosanthis Radix is found to contain bryonolic acid, 4-hydroxybenzoic acid, α-spinastero as sterols [Research Archives of Useful Plants Resources in Korea, Korea Research Institute of Chemical Technology, pp 354-357 (1988), 2. An Explanatory Diagram of Korean Medicinal Plants, Youngrim Pub., pp 960-963 (1990)].

Prunellae Spica, a flower or upper part of *Prunella vulgaris* and the same genera in plant taxonomy, is a non-toxic medicinal herb prepared by collecting the flower, when it is half withered during summer, and drying in the sun. Prunellae Spica has been widely used for the treatment of the following symptoms: chronic swellings, smallpox, acute mastitis and lymphatic tuberculosis. Prunellae Spica is also effective in the destructing lumps (generated in a lower stomach owing to extravasated blood) or others, while treating beriberi and numbness in the extremities. It has been reported that Prunellae Spica contains saponins such as oleanolic acid glycosides and ursolic acid glycosides, etc, and also contains carotene, vitamin C, vitamin K, tannin, caffeic acid and chlorogenic acid. Rosmarinic acid is also found in Prunellae Spica [Research Archives of Useful Plant Resources in Korea, Korea Research institute of Chemical Technology, pp 480-482 (1988); Chemical Research for Prunellae Spica, Lee Jakpyung et al., Bulletin of Medical College in Beijing, 17(4), pp 297-299 (1985); *Pharm. Acta. Helv.*, 66, No. 7, pp 185-188 (1991)].

The conventional oriental herbal books (e.g., Dong-Eui-Bo-gam, Hyangyak Gibsung-bang and Kwangjee Beakub) or related literatures refer to the medical efficacy of herbs and processes of manufacturing aqueous herbal solutions. However, they only described a single prescription of each of these medicinal plants but not a formulation available for the manufacture of aqueous herbal solution from appropriate combinations of sorted medicinal plants by harvest place and harvest time to control the content of active ingredients. Furthermore, these medicinal plants were prepared by hot water extraction method, and any substances extracted by above method showed no acquisition of detailed knowledge on biologically active ingredients.

On the other hand, the inventors of the present invention have disclosed a process of extraction and purified biologically effective ingredients from an extract of Clematis Radix, Trichosanthis Radix, and Prunellae Spica in a certain ratio, being useful for alleviating acute/chronic inflammation; for inhibiting platelet and whole blood aggregation, enzyme activities associated with degradation of joint tissue, abnormally proliferated immunocytes, and inflammation-inducing enzymes; for scavenging activity of toxic active oxygen radical; and further for the treatment of chronic rheumatoid arthritis (U.S. Pat. No. 5,910,307). U.S. Pat. No. 5,910,307 is characterized by mixing Clematis Radix, Trichosanthis Radix, and Prunellae Spica in a weight ratio of 1:0.5-2:0.5-1.5 and extracting the mixture with water or aqueous alcoholic solution; partitioning with water-saturated n-butanol and concentrating the alcohol layer under reduced pressure; and concentrating the result with water under constant boiling and lyophilizing to obtain an extract in powder form.

In the continuous study, the inventors have realized that it is difficult to standardize the extracts of Clematis Radix, Trichosanthis Radix, and Prunellae Spica with simple weight ratio since the content variation of each ingredient significantly varies with harvest place and harvest time. This further makes it difficult to merchandize such combined extracts since it is hard to obtain the reproducibility of active ingredients having analgesic and anti-inflammatory effects, blood circulation enhancing effect, arthritis therapeutic effect and cartilage protection. Thereupon, the inventors have made an extensive research to maximize the pharmacological efficiency of herbal drug composition with the reproducibility. As a result, we have developed a method to optimize the efficiency of cartilage protection effect as well as the analgesic and anti-inflammatory effect, blood circulation enhancing effect, and arthritis therapeutic effect by controlling the content of rosmarinic acid in the herbal drug composition, not the extract weight ratio of Clematis Radix, Trichosanthis Radix, and Prunellae Spica. In addition, it was possible to merchandize medicinal herbs with the reproducibility.

The present invention, an improved invention of U.S. Pat. No. 5,910,307, provides significant improvement in merchandizing by optimizing the herbal extract composition of Clematis Radix, Trichosanthis Radix, and Prunellae Spica with the proper content of rosmarinic acid, maximizes pharmacological efficiencies over the conventional herbal composition and further provides novel therapeutic effects.

SUMMARY OF THE INVENTION

The present invention is to provide a herbal drug composition comprising Clematis Radix, Trichosanthis Radix, and Prunellae, wherein the ingredients extracted and purified are standardized and merchandized based on the content of rosmarinic acid for the purpose of reproducibility and useful for an anti-inflammatory agent with analgesic effects, blood circulation enhancer, arthritis therapeutic agent and cartilage protective, etc. The herbal drug composition of the present invention has similar or superior efficiency for analgesic and anti-inflammatory effect and improving blood circulation to the conventional herbal composition of U.S. Pat. No. 5,910,307. In addition to that, it has excellent inhibitory activities against enzymes associated with degradation of joint tissue and a protection activity toward cartilage and thus, it is superiorly effective to general arthritis including rheumatism.

Accordingly, the object of the present invention is to provide a herbal drug composition having excellent analgesic and anti-inflammatory effect, improving effect of peripheral blood circulation, arthritis therapeutic effect and cartilage protection effect by standardizing the extracts from mixed Clematis Radix, Trichosanthis Radix, and Prunellae Spica with the proper content of rosmarinic acid.

DETAILED DESCRIPTION OF THE INVENTION

Figure 1:
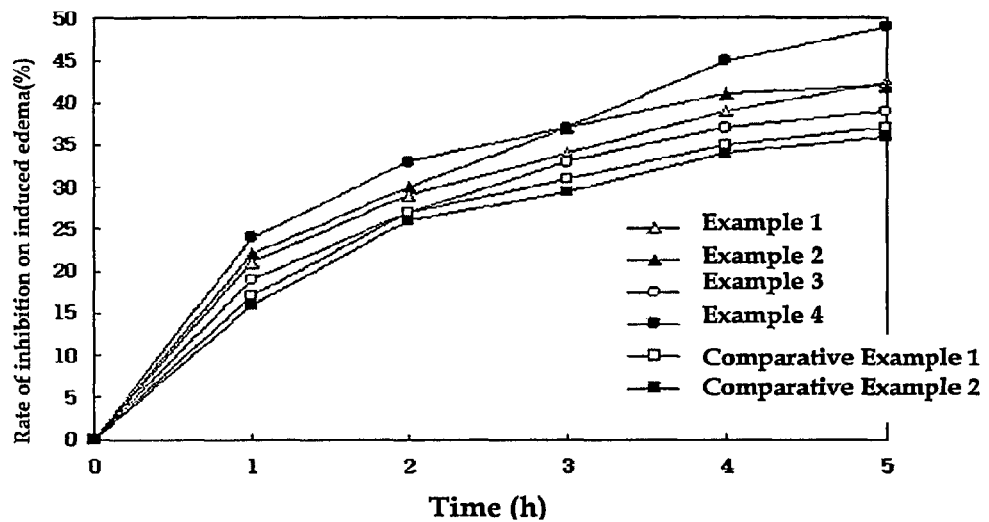
FIG. 1 represents the inhibitory activity of the herbal drug composition on edema induced by carrageenan.

The present invention is characterized by a combined herbal drug composition comprising Clematis Radix, Trichosanthis Radix, Prunellae Spica and more than 0.6 wt. % of rosmarinic acid based on the total composition.

The present invention is described in detail as set forth hereunder.

The herbal drug composition of the present invention provides significant biological effects such as analgesic and anti-inflammations, improvement of blood circulation, immunoregulation and inhibitions on enzymes associated with degradation of joint tissue, and particularly, cartilage protection and thus, being useful as arthritis therapeutic agent and cartilage protective as well as an analgesic and anti-inflammatory agent and blood circulation enhancer.

The content of active ingredients in herbal drugs varies remarkably with harvest place, harvest time, storage period and storage condition. Therefore, it is desirable to combine herbal extracts or herbal plants in an appropriate ratio depending on the harvest place as shown in Tables 1 to 3. That is, if harvest place, harvest time, storage period and storage condition are different, the content of active ingredients contained in the same weight of herbal plant has different contents, thus the limitation with the weight ratio of herbal extracts or herbal plants becomes insignificant.

Therefore, the present invention is characterized by selecting rosmarinic acid as a reference material to obtain the herbal drug composition with optimal pharmacological efficiency. Rosmarinic acid is known to have excellent activities such as: (i) antioxidant activity by inhibiting lipid peroxidation and/or biosynthesis of prostacyclin generated in the metabolism of arachidonic acid, and by scavenging the active oxygen generated from polymorphonuclear leukocytes; (ii) anti-inflammatory activity such as inhibition against the generation of metabolites which are carriers for inflammation reaction and immunoregulation to inhibit allergic inflammation; (iii) blood circulation enhancing activity by inhibition of platelet blood aggregation and fiber degradation [*Agent and Action*, 17, pp 375-376 (1985); *Pharm. Acta. Helv.*, 66, No. 7, pp 185-188 (1991); *Biochem. Pharmae.*, 29, pp 533-538 (1980); *Yoa-Hsueh-Hseuh-Pao*, 27, pp 96-100 (1992); *Int. J. of Immunopharmae.*, 10, No. 6, pp 729-737 (1988); *J. of Natural Products*, 50, No. 3, pp 392-399 (1987); *Yoa-Hsueh-Hseuh-Pao*, 28, No. 4, pp 241-245 (1993)]. The variation of a rosmarinic acid content is broad depending on harvest place, harvest time, storage period and storage condition etc. and further the efficiency varies with the content of rosmarinic acid. This is the reason why rosmarinic acid is selected as a reference material in the present invention. Accordingly, the herbal drug composition of the present invention can be prepared by mixing the herbal extracts of Clematis Radix, Trichosanthis Radix, Prunellae Spica or extracting the mixture of Clematis Radix, Trichosanthis Radix, Prunellae Spica not depending on the weight ratio of each herbal plant but depending on the content of rosmarinic acid contained in the total herbal plants.

The herbal drug composition can obtain the desired pharmaceutical efficiencies when the content of rosmarinic acid is higher than 0.6 wt. % of rosmarinic acid, preferably 0.6-5.0 wt. %. When the content of rosmarinic acid is higher than 0.6 wt. % in the herbal drug composition comprising Clematis Radix, Trichosanthis Radix, Prunellae Spica, it provides optimal effects such as cartilage protection activity which has not been taught in the conventional herbal drug compositions as well as alleviation of pains, improvement of blood circulation, immunoregulation, and inhibition of enzymes associated with degradation of joint tissue. If the content of rosmarinic acid is lower than 0.6 wt. %, the herbal drug composition provides alleviation of pains, improvement of blood circulation, immunoregulation, and inhibition of enzymes associated with degradation of joint tissue but very sluggish cartilage protection activity. The present invention has no upper limitation for the amount of the rosmarinic acid but when it is higher than a certain level, the activities are not improved any further, thus it is not desirable technically and economically to increase the content of rosmarinic acid to higher than a certain level.

According to the present invention, when the herbal drug composition contains 2.0-6.0 wt. % of oleanolic acid and 0.01-0.04 wt. % of 4-hydroxybenzoic acid in addition to higher than 0.6 wt. % of rosmarinic acid, it provides far more potent efficacy toward cartilage protection activity as well as alleviation of pains, improvement of blood circulation, immunoregulation, and inhibition of enzymes associated with degradation of joint tissue.

Large quantity of oleanolic acid is present in the extract of Clematis Radix. When the extract is hydrolyzed, sufficient amounts of oleanolic acid are present as a sapogenin, a sugar-free form of saponins. According to an analysis, it is found that oleanolic acid is present as saponins bonded to various glycosides. It has been reported that oleanolic acid has not only remarkable anti-inflammatory and analgesic effects but also an excellent effect for chronic rheumatoid arthritis induced by Mycobacterium butyricum. [*J. of Pharm. Pharmacol.*, 44, No. 5, pp 456-458 (1992); *Chung-Kuo-Li-Hsueh-Pao*, 10, No. 4, pp 381-384 (1984); *Chem. Pharm, Bull.*, 28, No. 4, pp 1183-1188 (1980); *Biochem. Int.*, 24, No. 5, pp 981-990 (1991)].

The extract of Trichosanthis Radix contains various organic acids including 4-hydroxybenzoic acid. 4-hydroxybenzoic acid is known to have excellent anti-oxidant activity, anti-inflammatory activity and hormone-like effect in the uterus ablation osteoporotic model and further is one of reference materials for the present invention because it is maintained in a certain amount regardless of harvest place, harvest time, storage period and storage conditions [*Free Radical Biol. & Medcine*, 27, No. 11/12, pp 1427-1436 (1999); *J. Ethnopharma.*, 53, 11-14 (1996); *Environ. Res.*, 75, pp 130-134 (1997)].

Rosmarinic acid, oleanolic acid and 4-hydroxybenzoic acid selected as reference materials are active ingredients of herbal drug composition obtained from this invention. The efficacy is far more potent due to remarkable synergic effect when they are combined in a certain ratio based on the contents of active ingredients. Further, in addition to such active ingredients of the herbal drug composition from this invention, other different ingredients cannot be ruled out in this invention.

To contain certain amounts of reference materials, the herbal drug composition of the present invention is prepared by either mixing each extract in powder form of Clematis Radix, Trichosanthis Radix, and Prunellae or extracting the mixture of Clematis Radix, Trichosanthis Radix, and Prunellae Spica based on the chemical analysis of original herbal plants. The method for preparing herbal drug composition makes a little difference in cartilage protection activity. The method for preparing herbal drug composition is described in detail as set forth hereunder.

Each Clematis Radix, Trichosanthis Radix, and Prunellae Spica or a mixture thereof is extracted with 5-10 volumes of water or aqueous alcoholic solution under reflux for 4 to 6 hours and filtered. The filtrate is further extracted with 5-10 volumes of water or aqueous alcoholic solution under reflux and filtered. Each extract is combined and concentrated to dryness. Hence, if a small amount of the solvent is used, the extraction efficiency is low due to the lower solubility of extract and the difficulty of stirring the extract. In case of using an excess of the solvent, however, a larger amount of solvent saturated with lower alcohol in water has to be evaporated and removed, therefore which is uneconomical and difficult in handling. The present invention performs a series of extraction steps, i.e., first and second extraction, because when the extraction is on a large scale, significant losses are anticipated due to high contents of water in medicinal plants, in spite of effective filtration. So the second extraction is responsible for preventing the reduced extraction efficiency rather than the first extraction only. Further, it is revealed that about 85-95% of the total extract amount is obtained through two extractions. It is also found that more than three steps of extraction are not to be desirable in economical matter.

The extracts are filtered and concentrated, and the filtrate is purified to remove some impurities such as proteins, polysaccharides and fatty acids by extracting with the same amount of lower alcohol saturated with 3-4 volumes of water. Examples of lower alcohol used in the present invention include butyl alcohol and propyl alcohol. If the amount of water-saturated lower alcohol is less than that of the filtrate, a higher concentration of impurities (e.g., polysaccharides, and proteins) having relatively strong polarity causes lower concentration of active ingredients in the extracts due to poor separation of layers.

After separating the layers, the obtained fractions extracted with alcohol are concentrated under reduced pressure at 60-70° C. to remove lower alcohol in the sample. Then, the extract is further concentrated 2-3 times under constant boiling with 25-50 volumes of water to the total extract amount and followed with another same amount of water for homogeneous suspension. The reason why the residue is concentrated under constant boiling with water is to control the contents of remaining lower alcohol so as to use the extracting solution as pharmaceutical raw materials. The obtained extract is then lyophilized to give an extract powder.

The obtained extract powder has significant pharmacological effects, such as analgesic and anti-inflammatory agents, blood circulation enhancers, rheumatoid arthritis therapeutic agents, and cartilage protection agents.

Based on the general manufacturing method, the powdered extract of this invention is formulated in oral or parenteral administration such as tablets, soft gelatin capsules, injection solutions, ointments, and transdermals.

For human use, the herbal drug composition of this invention can be administered alone, but will generally be administered in admixture with a pharmaceutical carrier selected with regard to the intended route of administration and standard pharmaceutical practice. For example, the herbal drug composition may be administered orally, buccally or sublingually, in the form of tablets containing excipients such as starch or lactose, or in capsules or ovules either alone or in admixture with excipients, or in the form of elixirs or suspensions containing flavoring or coloring agents. Such liquid preparations may be prepared with pharmaceutically acceptable additives such as suspending agent (e.g., methylcellulose, a semi-synthetic glyceride such as witepsol or mixtures of glycerides such as a mixture of apricot kernel oil and PEG-6 esters or mixtures of PEG-8 and caprylic/capric glycerides). A compound may also be injected parenterally, for example intravenously, intramuscularly, subcutaneously or intracoronarily. For parenteral administration, the compound is best used in the form of a sterile aqueous solution that may contain other substances, for example salts, or monosaccharides such as mannitol or glucose, to make the solution isotonic with blood.

For administration to man, the effective dose of the herbal drug composition may vary with the age, weight, physical condition and response of the particular patient and administration may be made once a day or a few times a day according to the physician. Preferred dosages for an average adult patient (70 Kg) are as follows: in the range of from 50 to 2400 mg daily for oral administration such as individual tablets or capsules; in the range of from 50 to 400 mg daily for parenteral administration; in the range of from 300 to 2400 mg daily for ointments; and in the range of from 150 to 1200 mg daily for transdermal administration. The above dosages are exemplary of the average case but there can be individual instances in which higher or lower dosage ranges may be merited, and such are within the scope of this invention. Further, if the daily dosages of the herbal drug composition are less than the above ranges, the desired effects are not obtained. On the other hand, if they are higher than the above ranges, it is also not preferable due to toxic side effects.

In particular, while the herbal drug composition of the present invention was administered to human, the toxic side effect is far less than other chemically synthesized drugs. As a matter of fact, several toxicological tests reveal that the combined extract of the present invention is not toxic to the human.

The present invention is explained in more detail with reference to the following examples that should not be taken to limit the scope of the invention.

REFERENCE EXAMPLE 1

250 g of well air dried Clematis Radix where debris were removed by washing with water was extracted from 2 l of 30% (v/v) ethanol-containing water under reflux for 6 hrs while stirring. After filtration, the residue was extracted again from 1.5 l of 30% (v/v) ethanol-containing water under reflux for 6 hrs while stirring. The filtrates were combined and concentrated to have 1 l of the total volume. The filtrate was extracted with a same volume of water-saturated n-butanol three times. The n-butanol layers were combined and concentrated under reduced pressure at 60-70° C. to dryness. 0.3 l of water was added to the residue and extracted under constant boiling and repeated the procedure twice. The extract was well suspended in the same amount of distilled water and lyophilized to give powdered extract.

Other Clematis Radix harvested in different places were prepared by the above procedure and analyzed by high performance liquid chromatography. The result was summarized in Table 1 with the content (%) of oleanolic acid.

TABLE 1

| Harvest place (China) | Content of oleanolic acid (%) | Yield (%, w/w) |
| --- | --- | --- |
| Heilongjiang A | 6.98 | 3.25 |
| Heilongjiang B | 13.59 | 3.95 |
| Heilongjiang C | 2.68 | 2.76 |
| Jilin A | 9.29 | 2.58 |
| Jilin B | 0.12 | 4.05 |
| Jilin C | 8.96 | 2.94 |
| Liaoning A | 8.53 | 3.08 |
| Liaoning B | 6.75 | 2.83 |
| Liaoning C | 3.97 | 1.79 |
| Sichuan A | 0.15 | 3.64 |
| Sichuan B | 6.98 | 2.36 |

* A, B, C represent different places

REFERENCE EXAMPLE 2

250 g of well air dried Trichosanthis Radix where debris were removed by washing with water was extracted from 2.5 l of 30% (v/v) ethanol-containing water under reflux for 4 hrs while stirring. After filtration, the residue was extracted again from 1.5 l of water under reflux for 3 hrs while stirring. The filtrates were combined and concentrated to have 1 l of the total volume. The filtrate was extracted with a same volume of water-saturated n-butanol three times. The n-butanol layers were combined and concentrated under reduced pressure at 60-70° C. to dryness. 0.2 l of water was added to the residue and extracted under constant boiling and repeated the procedure twice. The extract was well suspended in the same amount of distilled water and lyophilized to give powdered extract.

Other Trichosanthis Radix harvested in different places were prepared by the above procedure and analyzed by high performance liquid chromatography. The result was summarized in Table 2 with the content (%) of rosmarinic acid.

TABLE 2

| Harvest place (China) | Content of rosmarinic acid (%) | Yield (%, w/w) |
| --- | --- | --- |
| Henan A | 3.13 | 2.17 |
| Henan B | 12.05 | 2.28 |
| Henan C | 8.34 | 2.06 |
| Hubei A | 1.89 | 2.40 |
| Hubei B | 7.22 | 3.20 |
| Hubei C | 5.75 | 1.52 |
| Hunan A | 10.96 | 2.74 |
| Hunan B | 4.89 | 1.92 |
| Hunan C | 13.00 | 3.19 |
| Sichuan A | 6.14 | 1.32 |
| Sichuan B | 12.45 | 1.40 |
| Sichuan C | 1.59 | 2.82 |

* A, B, C represent different places

REFERENCE EXAMPLE 3

250 g of well air dried Prunellae Spica having a length of 2.0-4.0 cm where debris were removed by washing with water was extracted from 2 l of water under reflux for 5 hrs while stirring. After filtration; the residue was extracted again from 2 l of water under reflux for 3 hrs while stirring. The filtrates were combined and concentrated to have 1 l of the total volume. The filtrate was extracted with a same volume of water-saturated n-butanol three times. The n-butanol layers were combined and concentrated under reduced pressure at 60-70° C. to dryness. 0.1 l of water was added to the residue and extracted under constant boiling and repeated the procedure twice. The extract was well suspended in the same amount of distilled water and lyophilized to give powdered extract.

Other Trichosanthis Radix harvested in different places were prepared by the above procedure and analyzed by high performance liquid chromatography. The result was summarized in Table 3 with the content (%) of 4-hydroxybenzoic acid.

TABLE 3

| Harvest place (China) | Content of 4-hydroxybenzoic acid (%) | Yield (%, w/w) |
| --- | --- | --- |
| Hebei A | 0.018 | 0.95 |
| Hebei B | 0.024 | 0.76 |
| Hebei C | 0.037 | 0.82 |
| Henan A | 0.047 | 0.91 |
| Henan B | 0.058 | 1.05 |
| Henan C | 0.019 | 0.064 |
| Anhui A | 0.041 | 0.71 |
| Anhui B | 0.058 | 1.23 |
| Anhui C | 0.098 | 0.86 |
| Zhejiang A | 0.045 | 0.79 |
| Zhejiang B | 0.073 | 1.08 |
| Zhejiang C | 0.062 | 1.19 |

* A, B, C represent different places

EXAMPLE 1

Preparation of a Mixture of the Herbal Drug Extracts

Clematis Radix, Trichosanthis Radix, and Prunellae Spica having 1.5% (w/w) of rosmarinic acid, 3.5% (w/w) of oleanolic acid, and 0.02% (w/w) of 4-hydroxybenzoic acid were mixed and n-butanol fractionation was performed three times, respectively. The extract obtained each step was combined and well suspended in the same amount of distilled water and lyophilized to give powdered extract.

EXAMPLE 2

Preparation of a Mixture of the Herbal Drug Extracts

Clematis Radix, Trichosanthis Radix, and Prunellae Spica having 0.7% (w/w) of rosmarinic acid, 5.0% (w/w) of oleanolic acid, and 0.01% (w/w) of 4-hydroxybenzoic acid were mixed and n-butanol fractionation was performed three times, respectively. The extract obtained each step was combined and well suspended in the same amount of distilled water and lyophilized to give powdered extract.

EXAMPLE 3

Preparation of a Mixture of the Herbal Drug Extracts

Clematis Radix, Trichosanthis Radix, and Prunellae Spica having 4.0% (w/w) of rosmarinic acid, 2.0% (w/w) of oleanolic acid, and 0.04% (w/w) of 4-hydroxybenzoic acid were mixed and n-butanol fractionation was performed three times, respectively. The extract obtained each step was combined and well suspended in the same amount of distilled water and lyophilized to give powdered extract.

EXAMPLE 4

Preparation of a Herbal Extract of Mixed Plants 200 g of well dried Clematis Radix harvested in Heilongjiang A where debris were removed by washing with water, 450 g of Trichosanthis Radix harvested in Henan A with a length of 2.0-4.0 cm, and 350 g of Prunellae Spica harvested in Henan B were mixed and the mixture was extracted with 10 l of water under reflux for 6 hrs. After filtration, the residue was extracted again from 7 l of water under reflux for 3 hrs while stirring. The filtrates were combined and concentrated to give 5 l of the total volume. The filtrate was extracted with the same volume of water-saturated n-butanol three times. The n-butanol layers were combined and concentrated under reduced pressure at 60-70° C. to dryness. One liter of water was added to the residue and extracted under constant boiling and repeated the procedure twice. The extract was well suspended in the same amount of distilled water and lyophilized to give powdered extract.

The powdered extract was determined by HPLC analysis having 2.1% (w/w) of rosmarinic acid, 2.1% (w/w) of oleanolic acid, and 2.5% (w/w) of 4-hydroxybenzoic acid.

COMPARATIVE EXAMPLE 1

Well dried Clematis Radix harvested in Heilongjiang B where debris were removed by washing with water, 500 g of Trichosanthis Radix harvested in Anhui C with a length of 2.0-4.0 cm, and 250 g of Prunellae Spica harvested in Hubei A were mixed and the mixture was extracted with 15 l of water under reflux for 6 hrs. After filtration, the residue was extracted again with 7 l of water under reflux for 3 hrs while stirring. The filtrates were combined and concentrated to give 5 l of the total volume. The filtrate was fractionated with the same volume of water-saturated n-butanol three times. The n-butanol layers were combined and concentrated under reduced pressure at 60-70° C. to dryness. One liter of water was added to the residue and extracted under constant boiling and the procedure was repeated twice. The extract was well suspended in the same amount of distilled water and lyophilized to give powdered extract.

The powdered extract was determined by HPLC analysis having 0.4% (w/w) of rosmarinic acid, 6.8% (w/w) of oleanolic acid, and 0.05% (w/w) of 4-hydroxybenzoic acid.

COMPERATIVE EXAMPLE 2

Preparation of a Mixture of Herbal Drug Extract

Each extract of Clematis Radix, Trichosanthis Radix, and Prunellae Spica prepared in Reference Examples 1, 2, and 3 was mixed and dissolved in aqueous alcoholic solution to have the contents of 0.45% (w/w) of rosmarinic acid, 6.11% (w/w) of oleanolic acid, and 0.02% (w/w) of 4-hydroxybenzoic acid. The mixture was concentrated under reduced pressure. The extract was well suspended in the same amount of distilled water and lyophilized to give powdered extract.

EXPERIMENTAL EXAMPLE 1

Test for Analgesic Effects

To investigate the analgesic effects of various extracts prepared by said Examples 1-4 and Comparative Examples 1-2, writhing test was conducted as presented in the following experimental method and the result was expressed as Table 4.

Experimental Method

The herbal extracts, prepared by said Examples 1-4 and Comparative Examples 1-2, were orally administered to ICR (Institute of Cancer Research) mice at doses of 200 mg or 400 mg per Kg of body weight.

One hour after administration, 0.6% (v/v) acetic acid was intraperitoneally injected to the animals at a volume of 0.1 ml per 10 g of body weight and from 5 minutes after administration, writhing frequency of each mice was observed for 10 minutes as a pain threshold.

TABLE 4

| Category | Dose of herbal drug extract (mg/Kg) | Avg. writhing frequency | Rate of inhibition (%) |
| --- | --- | --- | --- |
| Control | — | 19 | — |
| Example 1 | 200 | 12 | 36.8 |
|  | 400 | 9 | 52.6 |
| Example 2 | 200 | 11 | 42.1 |
|  | 400 | 8 | 57.9 |
| Example 3 | 200 | 11 | 42.1 |
|  | 400 | 9 | 52.6 |
| Example 4 | 200 | 10 | 47.4 |
|  | 400 | 7 | 63.2 |
| Comparative Example 1 | 200 | 13 | 31.6 |
|  | 400 | 10 | 47.4 |
| Comparative Example 2 | 200 | 14 | 26.3 |
|  | 400 | 11 | 42.1 |

According to the Table 4, it is revealed that the extract prepared by the present invention has superior analgesic effects from reduced writhing frequencies.

EXPERIMENTAL EXAMPLE 2

Test for Inhibitory Activity on Acute Inflammation

The inhibitory activity of the herbal extracts, prepared by said Examples 1-4 and Comparative Examples 1-2, on acute inflammation was investigated in rats. In comparison with the control, the anti-inflammatory effect on hind paw in edema was expressed as percent and the result is presented in the attached FIG. 1.

Experimental Method

The herbal extracts, prepared by said Examples 1-4 and Comparative Examples 1-2, was orally administered to white SD (Spraque-Dawley) rats. At one hour after administration, 0.1 ml of 1% carrageenan was intradermally injected to the left hind paw of rats and edema at that site was measured at 1 hour interval for 5 hours.

As noted in the attached in FIG. 1, it is revealed that the herbal extracts prepared by said Examples 1-4 of the present invention significantly inhibited the carrageenan-induced inflammation.

EXPERIMENTAL EXAMPLE 3

Test for the Anti-Aggregating Activity

Figure 2:
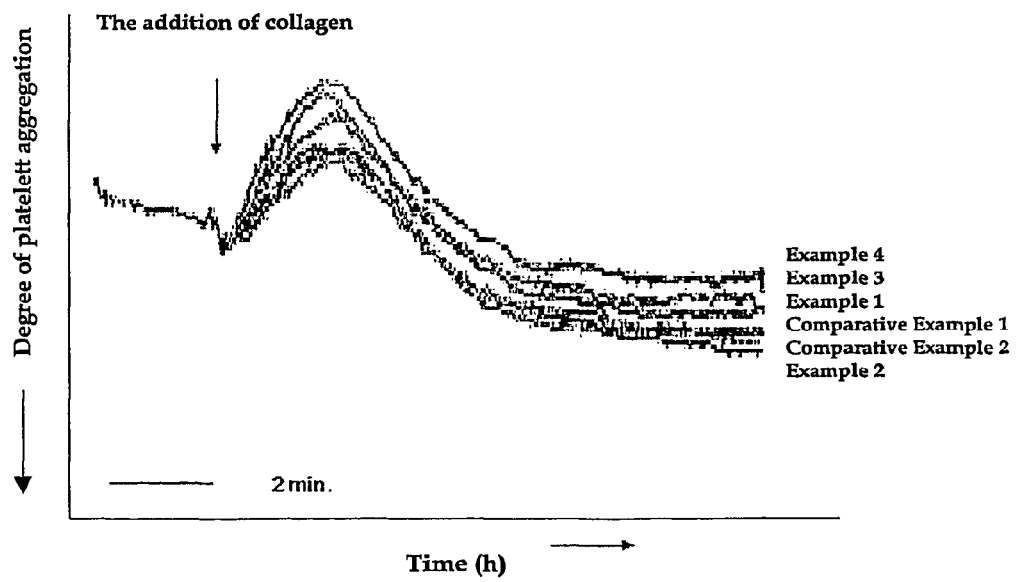
FIG. 2 represents the anti-coagulant activity of the herbal drug composition on platelet aggregation.

The anti-coagulant activity of the herbal extracts, prepared by said Examples 1-4 and Comparative Examples 1-2, was investigated in rabbits plasma and the aggregation was induced by collagen and the result is presented in the attached FIG. 2.

Experimental Method

PRP (platelet rich plasma) was prepared from the blood sample of rabbits and the number of platelet in blood was adjusted at $2 \times 10^8$/ml. The herbal extracts, prepared by said Examples 1-4 and Comparative Examples 1-2, were added to the PRP and adjusted on a cuvette of aggregometer at 37° C. for 2 minutes. With the addition of collagen platelet aggregation was measured with a dual aggregometer.

As noted in the attached FIG. 2, there was no increase in platelet aggregation by the herbal.

EXPERIMENTAL EXMPLE 4

Test for the Anti-Coagulant Activity on Whole Blood Coagulation

Figure 3:
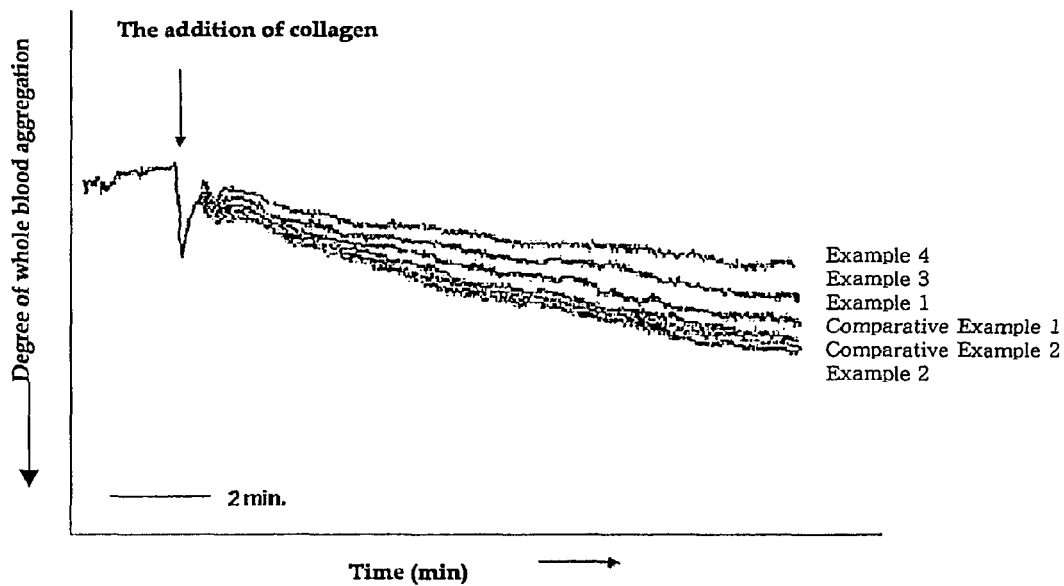
FIG. 3 represents the anti-coagulant activity of the herbal drug composition on whole blood aggregation.

The anti-coagulant activity of the herbal extracts, prepared by said Examples 1-4 and Comparative Examples 1-2, was investigated using whole blood of rabbit and the result is presented in the attached FIG. 3.

Experimental Method

The same amount of saline solution was added to whole blood of rabbit and mixed well prior to use in this experiment. The herbal extracts, prepared by said Examples 1-4 and Comparative Examples 1-2, were added to reconstituted whole blood and prewormed for 2 minutes. And, the blood coagulation was induced by the addition of collagen. The whole blood coagulation was measured by an aggregometer. As noted in the attached FIG. 3, there was no increase in whole blood coagulation when the herbal extracts prepared by said Examples 1-4 of the present invention was added.

EXPERIMENTAL EXAMPLE 5

Test for the Inhibitory Activity on Hyaluronidase, an Enzyme Associated with Degradation of Joint Tissue The inhibitory activity of the herbal extracts, prepared by said Examples 1-4 and Comparative Examples 1-2, on hyaluronidase, an enzyme associated with degradation of joint tissue, was investigated and the result is presented in the following Table 5.

Experimental Method

Hyaluronidase was prepared in the presence of acetate buffer solution at 37° C. for 20 minutes and activated. Then the herbal extracts, prepared by said Examples 1-4 and Comparative Examples 1-2, and potassium hyaluronate as a substrate were added to the buffer solution and cultured for about 40 minutes. After terminating the reaction with sodium hydroxide, potassium borate was added to the cultures and heated at 100° C. The absorbance was measured by the development of DMBA (dimethylbenzanthracene) and the rate of inhibition was calculated in comparison with control.

TABLE 5

| Category | Test concentration (mg/ml) | Rate of inhibition (%) |
|---|---|---|
| Example 1 | 1 | 82.3 |
| Example 2 | 1 | 83.7 |
| Example 3 | 1 | 89.6 |
| Example 4 | 1 | 87.5 |
| Comparative Example 1 | 1 | 80.5 |
| Comparative Example 2 | 1 | 79.1 |

As shown in Table 5, the combined herbal extracts prepared by the present invention significantly inhibited the activation of the enzyme associated with degradation of joint tissue.

EXPERIMENTAL EXAMPLE 6

Test for the Inhibitory Activity on Chronic Inflammation

The anti-inflammatory activity of the herbal extracts, prepared by said Examples 1-4 and Comparative Examples 1-2, on chronic rheumatoid arthritis was investigated in *Mycobacterium butyricum* injected rat models. The result is presented in the attached FIG. 4.

Experimental Method

To induce chronic edema, *Mycobacterium butyricum* suspended in mineral oil and treated with heat was injected to the right hind paw of white rats at each dose of 0.05 ml. Then, the herbal extracts, prepared by said Examples 1-4 and Comparative Examples 1-2, were orally administered to the rats once daily for 16 days, and the paw edema was measured with plethysmometer.

Figure 4:
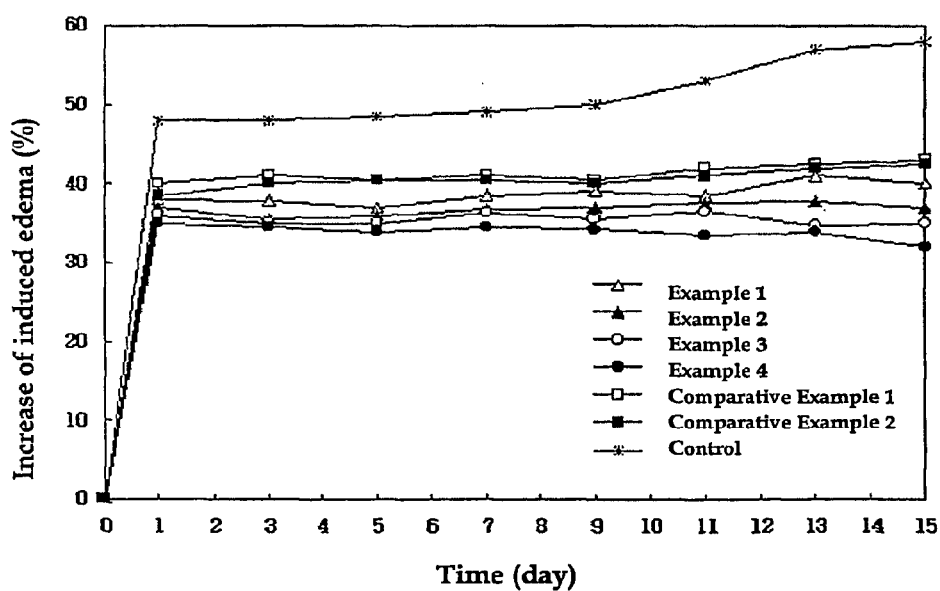
FIG. 4 represents the inhibitory activity of the herbal drug composition on chronic inflammation.

As shown in the attached FIG. 4, the combined herbal extracts by the present invention significantly inhibited the edema.

EXPERIMENTAL EXAMPLE 7

Test for the Inhibitory Activity on Leukotriene $B_4$

The inhibitory activity of the herbal extracts, prepared by said Examples 1-4 and Comparative Examples 1-2, on 5-lipoxygenase was evaluated by the inhibition rate of leukotriene $B_4$ ($LTB_4$) biosynthesis induced by arachidonic acid and calcium ionophore (A23187) and the result is presented in the Table 6.

Experimental Method

The extracts, prepared by said Examples 1-4 and Comparative Examples 1-2, were added to rat basophilic leukemia-1 (RBL-1) cells adjusted at 37° C. and reacted for 5 minutes. Then the reacting mixture was treated with 20 μg/ml A23187 and arachidonic acid for 15 minutes so as to induce the generation of $LTB_4$. The generated $LTB_4$ was extracted with ethyl acetate and was subjected to HPLC.

TABLE 6

| Category | Test concentration (mg/ml) | Rate of inhibition (%) |
|---|---|---|
| Example 1 | 0.5 | 87.3 |
| Example 2 | 0.5 | 82.5 |
| Example 3 | 0.5 | 79.1 |
| Example 4 | 0.5 | 85.7 |
| Comparative Example 1 | 0.5 | 71.5 |
| Comparative Example 2 | 0.5 | 70.6 |

As shown in the Table 6, the combined herbal extracts prepared by the present invention significantly inhibited 5-lipoxygenase.

EXPERIMENTAL EXAMPLE 8

Test for the Inhibitory Activity on Cyclooxygenase-I

The inhibitory activity of the herbal extracts, prepared by said Examples 1-4 and Comparative Examples 1-2 on cyclooxygenase-I was evaluated by arachidonic acid and the result is presented in the Table 7.

Experimental Method

The extracts, prepared by said Examples 1-4 and Comparative Examples 1-2, were added to cyclooxygenase-I adjusted at 37° C., and 100 μM arachidonic acid was added and reacted for 2 minutes, trichloroacetic acid (TCA) was added to the reacting mixture for terminating the reaction and absorbance was measured at 530 nm.

TABLE 7

| Category | Test concentration (mg/ml) | Rate of inhibition (%) |
|---|---|---|
| Example 1 | 0.5 | 61.8 |
| Example 2 | 0.5 | 62.5 |
| Example 3 | 0.5 | 59.8 |
| Example 4 | 0.5 | 67.3 |
| Comparative Example 1 | 0.5 | 51.5 |
| Comparative Example 2 | 0.5 | 49.1 |

As shown in the Table 7, the combined herbal extracts prepared by the present invention significantly inhibited cyclooxygenase-I.

EXPERIMENTAL EXAMPLE 9

Test for the Inhibitory Activity on Cyclooxygenase-II

The inhibitory activity of the extracts, prepared by said Examples 1-2 and 5 Comparative Examples 1-3, on cyclooxygenase-II was evaluated and the result is presented in the Table 8.

Experimental Method

The extracts prepared by said Examples 1-2 and Comparative Examples 1-3, were added to cyclooxygenase-II and placed at a test tube adjusted at 27° C. After reaction with 500 mM arachidonic acid for 90 seconds, trichloroacetic acid (TCA) was added to the reaction mixture for terminating the reaction and absorbance was measured at 532 nm.

TABLE 8

| Category | Test concentration (mg/ml) | Rate of inhibition (%) |
|---|---|---|
| Example 1 | 0.5 | 72.5 |
| Example 2 | 0.5 | 69.8 |
| Example 3 | 0.5 | 65.7 |
| Example 4 | 0.5 | 77.5 |
| Comparative Example 1 | 0.5 | 61.5 |
| Comparative Example 2 | 0.5 | 58.8 |

As shown in the Table 8, it is noted that the combined plant extracts prepared by this invention significantly inhibited cyclooxygenase-II.

EXPERIMENTAL EXAMPLE 10

Test for the Inhibitory Activity on the Proliferation of B-Lymphocyte

Figure 5:
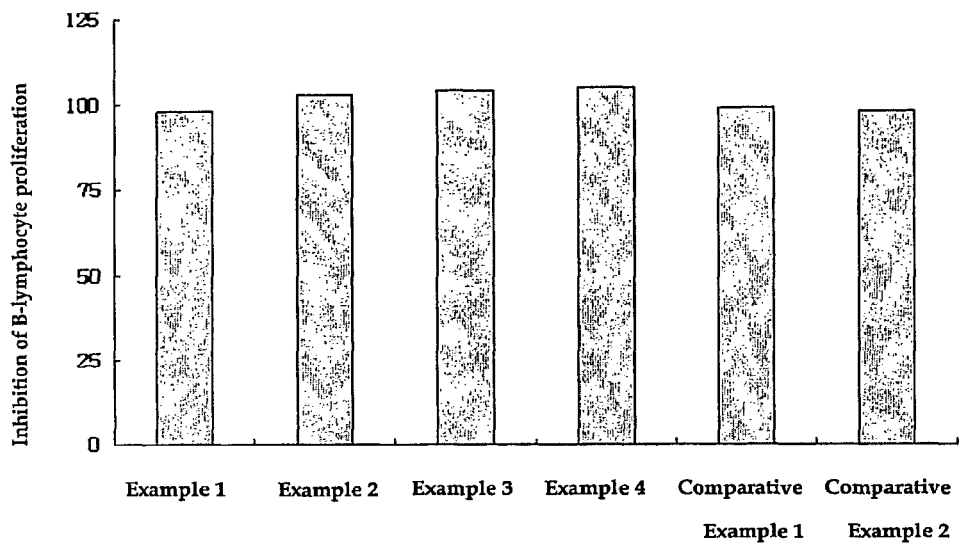
FIG. 5 represents the inhibitory activity of the herbal drug composition on B-lymphocyte proliferation.

The inhibitory activity of the herbal extracts, prepared by said Examples 1-4 and Comparative Examples 1-2 on the proliferation of B-lymphocyte induced by lipopolysaccharide (LPS) was evaluated and the result is presented in the attached FIG. 5.

Experimental Method

Cultures were set up with $10^6$ B-lymphocyte/ml of medium at 37° C. The extracts, prepared by said Examples 1-4 and Comparative Examples 1-2, were added to the cultures, and then the cultures were treated with 10 μg/ml of LPS for 24 hours. With the addition of 2 μCi Thymidine-$^3$H expressed by tritium as radioactivity for 48 hours, cultures were quantified on liquid scintillation counter (LSC).

As shown in the attached FIG. 5, it is noted that the combined herbal extracts prepared by the present invention significantly inhibited the proliferation of B-lymphocyte.

EXPERIMENTAL EXAMPLE 11

Test for the Inhibitory Activity on the Proliferation of T-Lymphocyte

Figure 6:
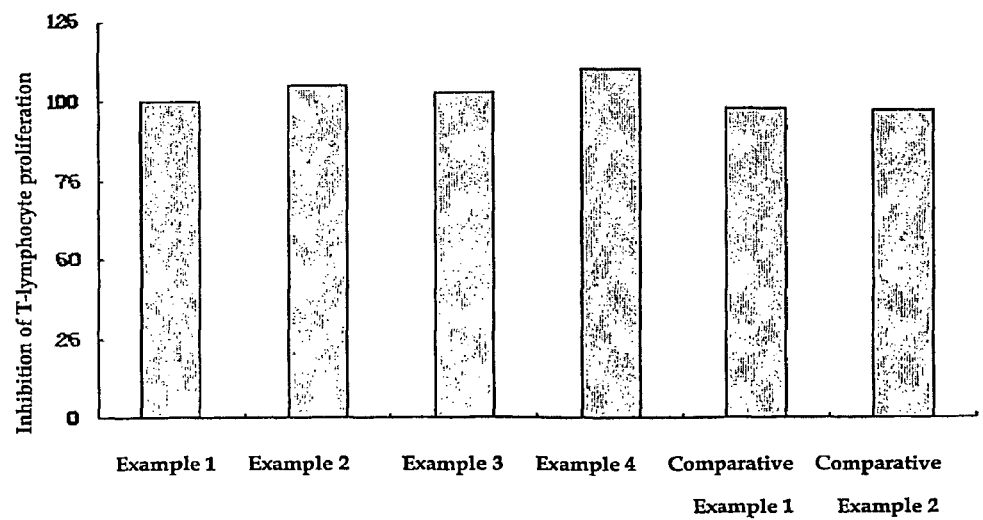
FIG. 6 represents the inhibitory activity of the herbal drug composition on T-lymphocyte proliferation.

The inhibitory activity of the herbal extracts, prepared by said Examples 1-4 and Comparative Examples 1-2, on the proliferation of T-lymphocyte induced by concanavalin-A (Con-A) were investigated and the result is presented in the attached FIG. 6.

Experimental Method

Cultures were set up with $10^6$ T-lymphocyte/ml of medium at 37° C. The extracts, prepared by said Examples 1-4 and Comparative Examples 1-2, were added to the cultures, which were treated with 3 µg/ml of concanavalin-A for 24 hours. With the addition of 2 µCi Thymidine-$^3$H expressed by tritium as radioactivity for 48 hours, cultures were quantified on LSC.

As shown in the attached FIG. 6, it is noted that the combined herbal extracts prepared by the present invention significantly inhibited the proliferation of T-lymphocyte.

EXPERIMENTAL EXAMPLE 12

Test for the Scavenging Activity on Elimination of Superoxide Radicals

The scavenging activity of the herbal extracts, prepared by said Examples 1-4 and Comparative Examples 1-2, was assessed on the elimination of superoxide radicals generated from xanthine-xanthine oxidase and the result is presented in the Table 9.

Experimental Method

Cytochrome-c (Cyt-c) and herbal extracts, prepared by Examples 1-4 and Comparative Examples 1-2, were added to xanthine oxidase adjusted at 37° C. so as to induce the generation of oxygen radicals by xanthine. The changes in color along with oxidation of cytochrome-c (Cyt-c) was measured by spectrophotometer at 540 nm and scavenging rate of oxygen radicals was also measured as slope.

TABLE 9

| Category | Test concentration (mg/ml) | Rate of inhibition (%) |
| --- | --- | --- |
| Example 1 | 0.5 | 82.7 |
| Example 2 | 0.5 | 89.5 |
| Example 3 | 0.5 | 83.6 |
| Example 4 | 0.5 | 92.1 |
| Comparative Example 1 | 0.5 | 81.5 |
| Comparative Example 2 | 0.5 | 78.4 |

As shown in the Table 9, it is noted that the combined herbal extracts prepared by the present invention significantly scavenged active oxygen.

EXPERIMENTAL EXAMPLE 13

Test for the Inhibitory Activity on Proteoglycan Degradation

The inhibitory activity of the herbal extracts, prepared by said Examples 1-4 and Comparative Examples 1-2, on the Proteoglycan degradation which is an important element in cartilage tissue was investigated and the result is presented in the Table 10.

Experimental Method

Cartilage from rabbits was dissected from each joint and 50 mg of cartilage was placed in a culture medium adjusted at 37° C. The herbal extract, prepared by said Examples 1-4 and Comparative Examples 1-2, and 5 µg of interleukin-1α (IL-1α) per 50 mg of cartilage were added to the culture medium and cultured for 72 hours. The production of glucosaminoglycan (GAG), which is produced by proteoglycan degradation, was measured at 525 nm by coloring with 1,9-dimethylmethylene blue dye.

TABLE 10

| Category | Test conc. (mg/ml) | Rate of inhibition on the proliferation of glucosaminoglycan (%) |
| --- | --- | --- |
| Example 1 | 1.0 | 115 |
|  | 0.3 | 83 |
|  | 0.1 | 68 |
| Example 2 | 1.0 | 103 |
|  | 0.3 | 91 |
|  | 0.1 | 79 |
| Example 3 | 1.0 | 99 |
|  | 0.3 | 81 |
|  | 0.1 | 73 |
| Example 4 | 1.0 | 121 |
|  | 0.3 | 94 |
|  | 0.1 | 75 |
| Comparative Example 1 | 1.0 | 84 |
|  | 0.3 | 52 |
|  | 0.1 | 38 |
| Comparative Example 2 | 1.0 | 81 |
|  | 0.3 | 46 |
|  | 0.1 | 37 |

As shown in the Table 10, it is noted that the combined herbal extracts prepared by the present invention significantly inhibited the proteoglycan degradation activity.

EXPERIMENTAL EXAMPLE 14

Test for the Inhibitory Activity on Type II Collagen Degradation

The inhibitory activity of the herbal extracts, prepared by said Examples 1-4 and Comparative Examples 1-2, on the Type II collagen degradation which is an important element in articular cartilage tissue was investigated and the result is presented in the Table 11.

Experimental Method

Cartilage from rabbits was dissected from each joint and 50 mg of cartilage was placed in a culture medium adjusted at 37° C. The herbal extract, prepared by said Examples 1-4 and Comparative Examples 1-2, and 5 µg of interleukin-1α (IL-1α) per 50 mg of cartilage were added to the culture medium and cultured for 21 days. The production of hydroxy proline, which is produced by type II collagen degradation, was measured at 560 nm by coloring with chloramines-T and dimethylaminobenzaldehyde.

TABLE 11

| Category | Test conc. (mg/ml) | Rate of inhibition on the proliferation of hydroxy-Proline (%) |
| --- | --- | --- |
| Example 1 | 1.0 | 91 |
|  | 0.3 | 63 |
|  | 0.1 | 38 |
| Example 2 | 1.0 | 89 |
|  | 0.3 | 59 |
|  | 0.1 | 39 |
| Example 3 | 1.0 | 97 |
|  | 0.3 | 76 |
|  | 0.1 | 53 |

TABLE 11-continued

| Category | Test conc. (mg/ml) | Rate of inhibition on the proliferation of hydroxy-Proline (%) |
|---|---|---|
| Example 4 | 1.0 | 93 |
|  | 0.3 | 65 |
|  | 0.1 | 46 |
| Comparative Example 1 | 1.0 | 67 |
|  | 0.3 | 36 |
|  | 0.1 | 19 |
| Comparative Example 2 | 1.0 | 65 |
|  | 0.3 | 36 |
|  | 0.1 | 20 |

As shown in the Table 11, it is noted that the combined herbal extracts prepared by the present invention showed more significant inhibitory activity on the Type II collagen degradation than that of Comparative Example 1.

EXPERIMENTAL EXAMPLE 15

Test for the Therapeutic Efficacy Against Osteoarthritis

The activity on osteoarthritis of the herbal extracts, prepared by said Examples 1-4 and Comparative Examples 1-2, on cartilage protection was investigated by monitoring rabbit models of which cartilage was injured by injecting collagenase to cavum articular of rabbit to have similar symptoms to human osteoarthritis. The result is presented in the Table 12.

Experimental Method 1 mg of collagenase per 1 Kg of body weight was injected at the first and fourth days to the cavum articular of rabbit having 2.0-2.5 Kg of body weight to injure joint tissue and to have collagenase-induced arthritis. The extracts, prepared by said example 1-4 and comparative example 1-2, were given orally at a dose of 200 mg/Kg for 4 weeks. After 4 weeks of administration, the cartilage part was dissected and withdrawn from the rabbit and then dyed with sapranin-O. The dyed cartilage part was divided into cartilaginous tissue and synovial tissue and the degree of arthritis severity was recorded with the integer scale of 0-4 to quantify the levels: 0=normal; 1=slight; 2=moderate; 3=severe; and 4=maximum.

TABLE 12

| Category | Cartilaginous tissue[1] | Synovial tissue[2] | Total[3] |
|---|---|---|---|
| Control | 11.8 | 10.8 | 21.6 |
| Example 1 | 6.0 | 6.5 | 12.5 |
| Example 2 | 6.2 | 7.2 | 13.4 |
| Example 3 | 6.3 | 7.1 | 13.4 |
| Example 4 | 5.0 | 6.0 | 11.0 |
| Comparative Example 1 | 8.6 | 8.2 | 16.8 |
| Comparative Example 2 | 8.7 | 8.0 | 16.7 |

[1] Cartilaginous tissue (score for complete arthritis: 24): Loss of superficial layer, Erosion of cartilage, Fibrillation and/or fissures, Disorganization of chondrocytes, Loss of chondrocytes, Cluster formation
[2] Synovial tissue (score for complete arthritis: 24): hyperplasia of synovial lining cell, hypertrophy of synovial lining layer, infiltration of inflammatory cells, proliferation of granulation tissue, vascularization
[3] Total (score for complete arthritis: 48)

As shown in the Table 12, it is noted that the combined herbal extracts prepared by the present invention showed more significant alleviation activity on collagenase-induced arthritis than that of Comparative Example 1.

MANUFACTURING EXAMPLE 1

The following chemical composition was employed for the manufacture of oral tablets using the powdered extracts of the present invention.
Chemical Composition: the herbal drug composition 200 mg; hard anhydrous silicate 10 mg; Magnesium stearate 2 mg; microcrystalline cellulose 50 mg; Sodium starch glycolate 25 mg; corn starch 113 mg; and anhydrous ethanol in an appropriate amount.

MANUFACTURING EXAMPLE 2

The following chemical composition was employed for the manufacture of ointments using the powdered extracts of the present invention.
Chemical Composition: the herbal drug composition 5 g; cetyl palmitate 20 g; cetyl alcohol 40 g; stearyl alcohol 20 g; isopropyl myristate 80 g; sorbitan monostearate 20 g; polysorbate 60 g; propyl p-hydroxybenzoate 1 g; methyl p-hydroxybenzoate 1 g; and phosphoric acid and distilled water in an appropriate amount.

MANUFACTURING EXAMPLE 3

The following chemical composition was employed for the manufacture of injection solutions using the powdered extracts of the present invention.
Chemical Composition: the herbal drug composition 100 mg; mannitol 180 mg; $Na_2HPO_4$ 25 mg; and water for injection 2,974 mg.

MANUFACTURING EXAMPLE 4

The following chemical composition was employed for the manufacture of transdermal using the powdered extracts of the present invention.
Chemical Composition 1: the herbal drug composition 0.4 g; poly(acrylic acid, sodium salt) 1.3 g; glycerin 3.6 g; aluminum hydroxide 0.04 g; methyl paraben 0.2 g; and water 14 g.
Chemical Composition 2: the herbal drug composition 0.8 g; propylene glycol 1.6 g; fluid paraffin 0.8 g;
Several dosage forms (e.g., tablets, ointments, transdermal and injection solutions) prepared by said manufacture 1-4 related to combined herbal preparations using Clematis Radix, Trichosanthis Radix and Prunellae Spica according to this invention. Said preparations contain concentrations of oleanolic acid and rosmarinic acid as reference materials, thus being effectively used for anti-inflammatory agent with analgesic effects, chronic rheumatoid arthritis drug and agent for improving peripheral blood circulation.

The invention claimed is:
1. An herbal drug composition for cartilage protection comprising extracts from Clematis Radix, Trichosanthis Radix, and Prunellae Spica, wherein:
rosmarinic acid is present in the range of from 0.7 to 5.0 wt % to the total composition; wherein said herbal drug composition further comprises oleanolic acid and 4-hydroxybenzoic acid; wherein:
said oleanolic acid is present in the range of from 2.0 to 6.0 wt. % of the total composition and said 4-hydroxybenzoic acid is present in the range of from 0.01 to 0.04 wt. % of the total composition.

2. The herbal drug composition of claim 1;
wherein the weight percentages of rosmarinic acid, oleanolic acid, and 4-hydroxybenzoic acid are pharmaceutically effective for cartilage protection and arthritis therapeutic treatment.

3. The herbal drug composition according to claim 1, wherein said composition is in the form of a tablet, a soft gelatin capsule, an injection solution, an ointment or a transdermal formulation.

4. The herbal drug composition according to claim 3, wherein the dose of said tablet or soft gelatin capsule is in the range of from 50 to 2,400 mg.

5. The herbal drug composition according to claim 3 comprising 200 mg of the extracts.

6. A method of providing cartilage protection which comprises administering a therapeutically effective amount of the herbal drug composition of claim 1 to a patient in need thereof.

7. The method of claim 6, wherein wt. % ratio of rosmarinic acid to 4-hydroxybenzoic acid is from 70:1 to 100:1.

8. The method of claim 7, wherein the cartilage protection is achieved via providing inhibitory activity against an enzyme associated with the degradation of joint tissue.

9. The method of claim 8, wherein the enzyme is hyaluronidase.

10. The method of claim 7, wherein the cartilage protection is achieved via inhibitory activity against proteoglycan degradation.

11. The method of claim 7, wherein the cartilage protection achieved via inhibitory activity against type II collagen degradation.

12. The method according to claim 6, wherein said herbal drug composition is administered orally at a range of from 50 to 2,400 mg daily.

13. The method according to claim 6, wherein said herbal drug composition is administered parenterally at a range from 50 to 400 mg daily.

14. The method according to claim 6, wherein said herbal drug composition is the form of an ointment and is administered from 300 to 2,400 mg daily.

15. The method according to claim 6, wherein said herbal drug composition is administered transdermally at a range from 150 to 1,200 mg daily.

16. The method according to claim 6, wherein said herbal drug composition is administered at 200 mg/Kg body weight or 400 mg/Kg body weight.

* * * * *